United States Patent [19]

Dore et al.

[11] Patent Number: 5,547,947
[45] Date of Patent: Aug. 20, 1996

[54] METHODS OF TREATMENT

[75] Inventors: Benoit T. Dore, Chateauguay; Richard L. Momparler, Montreal, both of Canada; Milan R. Uskokovic, Upper Montclair, N.J.

[73] Assignee: Hoffmann-La Roche Inc., Nutley, N.J.

[21] Appl. No.: 347,539

[22] Filed: Nov. 30, 1994

Related U.S. Application Data

[63] Continuation of Ser. No. 29,744, Mar. 11, 1993, abandoned.

[51] Int. Cl.$^6$ ............................................. A61K 31/59
[52] U.S. Cl. ................................................. 514/167
[58] Field of Search ..................................... 514/167

[56] References Cited

U.S. PATENT DOCUMENTS

| | | |
|---|---|---|
| 3,746,730 | 7/1973 | Marbet . |
| 4,358,406 | 11/1982 | Deluca et al. . |
| 4,613,594 | 9/1986 | Baggiolini et al. ............ 514/167 |
| 4,804,502 | 2/1989 | Baggiolini et al. ............ 260/397.2 |
| 5,087,619 | 2/1992 | Baggiolini et al. ............ 514/167 |

OTHER PUBLICATIONS

Proceedings of the American Association for Cancer Research vol. 34, Mar. 1993 p. 622.

Koga and Sutherland, Retinoic Acid Acts Synergistically With dihydroxyvitamin $D_3$ or Angioestrogen to Inhibit T–47 D Human Breast Cancer Cell Proliferation, J. Steroid. Biochem. Molec. Biol. vol. 39, No. 4A p. 455–60 (1991).

Proceedings of the American Assoication for Cancer Research vol. 34, Mar. 1993, Abstract 761.

Farach–Carson, et al., Nongenomic Actions of 1,25–Dihydroxy $D_3$ in Rat Osteosarcoma Cells: Structure Function Studies Using Ligand Analogs*: Endocrinology, vol. 129, No. 4, pp. 1876–1884 (1991).

Zhou, et al., Development of a Novel 1,25–(OH)$_2$–Vitamin $D_3$ Analog With Potent Ability to Induce HL–60 Cell Differentiation Without Modulating Calcium Metabolism: Blood, vol. 78, No. 1, pp. 75–82, Jul. 1, 1991.

Proceeding of Am Association for Cancer Research, vol. 34, Mar. 1993.

*Primary Examiner*—Jerome D. Goldberg
*Attorney, Agent, or Firm*—George W. Johnston; Ellen Ciambrone Coletti

[57] ABSTRACT

A method of inducing inhibition or loss of cell proliferation in solid tumors utilizing a Vitamin $D_3$ analog, as well as a method of inducing loss of cell proliferation in solid tumors utilizing trans retinoic acid and a Vitamin $D_3$ analog.

In another aspect, a method of inducing inhibition or loss of cell proliferation in solid tumors utilizing a Vitamin $D_3$ metabolite, as well as a method of inducing loss of cell proliferation in solid tumors utilizing trans retinoic acid and a Vitamin $D_3$ metabolite.

2 Claims, No Drawings

METHODS OF TREATMENT

This is a continuation, of application Ser. No. 08/029,744 filed Mar. 11, 1993 now abandoned.

BRIEF SUMMARY OF THE INVENTION

In one aspect, the invention relates to a method of inducing inhibition or loss of cell proliferation in breast tumors, which comprises administering to a host in need of such treatment an effective amount of a Vitamin $D_3$ analog. In another aspect, the invention relates to a method of inducing inhibition or loss of cell proliferation in breast tumors which comprises administering to a host in need of such treatment an effective amount of trans retinoic acid and a Vitamin $D_3$ analog. Preferably, the Vitamin $D_3$ analog is selected from the group consisting of 1α,25-dihydroxy-26,27-hexafluorocholecalciferol;

1α,25-dihydroxy-22-ene-26,27-hexafluorocholecalciferol;

1α,25-dihydroxy-26,27-hexafluoro-16-ene-23-yne-cholecalciferol;

1α,25-dihydroxy-23-yne-cholecalciferol;

1α,25-dihydroxy-16-ene-cholecalciferol;

1α,25-dihydroxy-16-ene-23-yne-cholecalciferol;

26,26,26,27,27,27-hexafluoro-25-hydroxy- 16-ene-23-yne-cholecalciferol;

26,26,26,27,27,27-hexafluoro-1α-fluoro-25-hydroxy-16-ene-23 -yne-cholecalciferol;

26,26,26,27,27,27-hexafluoro-1α,25-dihydroxy-16-ene-3-yne-19-nor-cholecalciferol;

26,26,26,27,27,27-hexafluoro-25-hydroxy-16-ene-23-yne-19-nor-cholecalciferol; and 6,26,26,27,27,27-hexafluoro-1α-fluoro-25-hydroxy-16-ene-23-yne-19-nor-cholecalciferol.

In yet another aspect, the invention relates to a method of inducing inhibition or loss of cell proliferation in breast tumors, which comprises administering to a host in need of such treatment an effective amount of a Vitamin $D_3$ metabolite, such as, 1α,25-dihydroxycholecalciferol (hereinafter also referred to as "$D_3$"), either alone or in combination with trans retinoic acid.

DETAILED DESCRIPTION OF THE INVENTION

Surprisingly, it has now been found that a beneficial inhibition or loss of cell proliferation in solid tumors can be achieved utilizing a Vitamin $D_3$ analog, especially one of those more particularly described hereinafter, alone or in combination with all trans retinoic acid (hereinafter also referred to as "RA").

Accordingly, the invention comprises a method of achieving an inhibition of or loss in cell proliferation in solid tumor in a host requiring such treatment by administering an effective amount of a Vitamin $D_3$ analog selected from the group consisting of 1α,25-dihydroxy-26,27-hexafluorocholecalciferol (hereinafter also referred to as "HF");

1α,25-dihydroxy-22-ene-26,27-hexafluorocholecalciferol (hereinafter also referred to as "22 HF");

1α,25-dihydroxy-26,27-hexafluoro-16-ene-23-yne-cholecalciferol (hereinafter also referred to as "16-23HF");

1α,25-dihydroxy-23-yne-cholecalciferol (hereinafter also referred to as "23D");

1α,25-dihydroxy-16-ene-cholecalciferol (hereinafter also referred to as "16D");

1α,25-dihydroxy-16-ene-23-yne-cholecalciferol (hereinafter also referred to as "16-23D");

26,26,26,27,27,27-hexafluoro-25-hydroxy-16-ene-23-yne-cholecalciferol;

26,26,26,27,27,27-hexafluoro-1α-fluoro-25-hydroxy-16-ene-23-yne-cholecalciferol (hereinafter also referred to as "1F-16-23HF");

26,26,26,27,27,27-hexafluoro-1α,25-dihydroxy-16-ene-23-yne-19-nor-cholecalciferol (hereinafter also referred to as "19 nor");

26,26,26,27,27,27-hexafluoro-25-hydroxy-16-ene-23-yne-19-nor-cholecalciferol; and 26,26,26,27,27,27-hexafluoro-1α-fluoro-25-hydroxy-16-ene-23-yne-19-nor-cholecalciferol.

The invention also comprises a method of inducing inhibition or loss of cell proliferation in breast tumors, which comprises administering to a host in need of such treatment an effective amount of a Vitamin $D_3$ metabolite, preferably, 1α,25-dihydroxycholecalciferol, either alone or in combination with retinoic acid.

A preferred group of Vitamin $D_3$ analogs, utilized in the methods of the invention, comprises the group:

1α,25-dihydroxy-26,27-hexafluorocholecalciferol;

1α,25-dihydroxy-22-ene-26,27-hexafluorocholecalciferol;

1α,25-dihydroxy-26,27-hexafluoro-16-ene-23-yne-cholecalciferol;

26,26,26,27,27,27-hexafluoro-25-hydroxy-16-ene-23-yne-cholecalciferol;

26,26,26,27,27,27-hexafluoro- 1α-fluoro-25-hydroxy-16-ene- 23 -yne-cholecalciferol;

26,26,26,27,27,27-hexafluoro-1α,25-dihydroxy-16-ene-23-yne-19-nor-cholecalciferol;

26,26,26,27,27,27-hexafluoro-25-hydroxy-16-ene-23-yne-19-nor-cholecalciferol; and 26,26,26,27,27,27-hexafluoro- 1α-fluoro-25-hydroxy-16-ene-23-yne-19-nor-cholecalciferol.

Preferred Vitamin $D_3$ analogs utilized in the methods of the invention are 1α,25-dihydroxy-26,27-hexafluoro-16-ene-23-yne-cholecalciferol; 1α,25-dihydroxy-26,27-hexafluorocholecalciferol; and 1α,25-dihydroxy-16-ene-23-yne-cholecalciferol.

A particularly preferred Vitamin $D_3$ analog, utilized in the methods of the invention, is 1α,25-dihydroxy-26,27-hexafluoro-16-ene- 23-yne-cholecalciferol.

Processes for preparing 1α,25-dihydroxy-26,27-hexafluorocholecalciferol are set forth in U.S. Pat. No. 4,358,406, issued Nov. 9, 1982 which is hereby incorporated by reference. Processes for preparing 1α,25-dihydroxy-22-ene-26,27-hexafluorocholecalciferol are set forth in U.S. Pat. No. 4,613,594, issued Sep. 23, 1986 which is hereby incorporated by reference. Processes for preparing 1α,25-dihydroxy-23-yne-cholecalciferol are set forth in U.S. Pat. No. 4,804,502, issued Feb. 14, 1989 which is hereby incorporated by reference. Processes for preparing 1α,25-dihydroxy-16-ene-cholecalciferol and 1α,25-dihydroxy-16-ene-23-yne-cholecalciferol are set forth in U.S. Pat. No. 5.087, 619, issued Feb. 11, 1992 which is hereby incorporated by reference. Processes for preparing all trans retinoic acid are set forth in U.S. Pat. No. 3.746.730, issued Jul. 17, 1973 which is hereby incorporated by reference. Processes for preparing 1α,25-dihydroxy-26,27-hexafluoro-16-ene-23-yne-cholecalciferol;

26,26,26,27,27,27-hexafluoro-25-hydroxy-16-ene-23-yne-cholecalciferol;

26,26,26,27,27,27-hexafluoro-1α-fluoro-25-hydroxy-16-ene-23-yne-cholecalciferol;

26,26,26,27,27,27-hexafluoro-1α,25-dihydroxy-16-ene-23-yne-19-nor-cholecalciferol;

26,26,26,27,27,27-hexafluoro-25-hydroxy-16-ene-23-yne-19-nor-cholecalciferol; and 26,26,26,27,27,27-hexafluoro-1α-fluoro-25-hydroxy-16-ene-23-yne-19-nor-cholecalciferol are set forth in U.S. patent application Ser. No. 971,788, filed Nov. 5, 1992, which is hereby incorporated by reference.

The methods of the invention can be utilized for the treatment of breast tumors, such as, those comprising MDA-MB231 cells which are devoid of estrogen receptors, T-47D cells which possess estrogen receptors and the like. The inhibition or loss in cell proliferation in solid tumors can be demonstrated utilizing the procedures described herein below.

A colony assay can be used to evaluate inhibition or loss of solid tumor cell proliferation on tumor cells with the Vitamin $D_3$ analogs or metabolites referred to herein, particularly, 1α,25-dihydroxycholecalciferol; 1α,25-dihydroxy-26,27-hexafluorocholecalciferol; 1α,25-dihydroxy-22-ene-26,27-hexafluoro-cholecalciferol; 1α,25-dihydroxy-26,27-hexafluoro-16-ene-23-yne-cholecalciferol; 1α,25-dihydroxy-16-ene-cholecalciferol; and 1α,25-dihydroxy-16-ene-23-yne-cholecalciferol.

METHOD

Cells of the cell line utilized are trypsinized, counted and plated 250 cells/5 ml minimal essential medium (MEM) containing 10% heat inactivated fetal calf serum. The test compound is added 48 hours after plating for an exposure time of 120 hours. Thereafter, the medium is aspirated and replaced with drug-free medium, and 14–16 days later the medium is aspirated. The colonies formed are fixed and stained with 0.5% methylene blue in 50% methanol. Colonies which contain greater than 500 cells are counted. The percent loss in colony formation is determined as follows:

$$\frac{(\text{\# of colonies produced in control}) - (\text{\# of colonies provided in treated group})}{\text{\# of colonies produced in control}} \times 100$$

TABLE I

EFFECT OF VITAMIN D ANALOGS ON COLONY FORMATION BY HUMAN BREAST CARCINOMA CELLS (T-47-D)

| Drug | Concentration (μM) | Exposure time (hr) | % loss in colony formation[a] |
|---|---|---|---|
| $D_3$ | 0.05 | 120 | 29* |
| $D_3$ | 0.1 | 120 | 94* |
| 16 $D_3$ | 0.01 | 120 | 30.5 ± 6.4 |
| 16-23 $D_3$ | 0.05 | 120 | 82.0 ± 11.3 |
| 23$D_3$ | 0.1 | 120 | 72.0 ± 29.7 |
| HF | 0.01 | 120 | 83.5 ± 12.0 |
| 22HF | 0.01 | 120 | 51.0 ± 45.2 |
| 16-23-$D_3$HF | 0.01 | 120 | 100 ± 0 |

[a]mean ± S.D. n = 2
*only one test was run at this concentration, accordingly no standard deviation is provided.

TABLE II

EFFECT OF VITAMIN D ANALOGS ON COLONY FORMATION BY HUMAN BREAST CARCINOMA CELLS (MDA-MB231)

| Drug | Concentration (μM) | Exposure time (hr) | % loss in colony formation[a] |
|---|---|---|---|
| $D_3$ | 0.1 | 120 | 25.0 ± 8.7 |
| 16 $D_3$ | 0.01 | 120 | 42.0 ± 20.5 |
| 16-23 $D_3$ | 0.05 | 120 | 30.0 ± 16.1 |
| 23$D_3$ | 0.1 | 120 | 33.3 ± 14.9 |
| HF | 0.01 | 120 | 23.7 ± 19.8 |
| 22HF | 0.01 | 120 | 29.0 ± 15.9 |
| 16-23-$D_3$HF | 0.01 | 120 | 26.7 ± 17.3 |

[a]mean ± S.E. n = 3

The synergistic compositions and methods of the invention can be utilized for the treatment of breast tumors. The inhibition or loss of solid tumor cell proliferation of the method of the invention comprising administering a combination of trans retinoic acid and Vitamin $D_3$ analogs or metabolites may be demonstrated utilizing the procedure described above. In order to determine if the interactions between the drugs was synergistic the data on colony formation were analyzed according to F. Valeriote and H. Lin, *Synergistic Interaction of Anticancer Agents: A cellular perspective*, Cancer Chemother. Rep. 59, 895 (1975). The results on percent loss in colony formation are presented in Tables III and IV below.

TABLE III

EFFECT OF ALL-TRANS RETINOIC ACID (RA) AND 16-23$D_3$ ON COLONY FORMATION BY HUMAN BREAST CARCINOMA CELLS (MDA-MB-231)

| Drug | Concentration (μM) | Exposure time (hr) | % loss in colony formation[a] |
|---|---|---|---|
| RA | 1.0 | 120 | 1.7 ± 0.9 |
| 16-23-$D_3$ | 0.05 | 120 | 30.0 ± 16.1 |
| RA + 16-23-$D_3$ | 1.0 + 0.05 | 120 | 55.7 ± 10.6 |

[a]mean ± S.E. n = 3

TABLE IV

EFFECT OF ALL-TRANS RETINOIC ACID (RA) AND 16-23$D_3$HF ON COLONY FORMATION BY HUMAN BREAST CARCINOMA CELLS (MDA-MB-231)

| Drug | Concentration (μM) | Exposure time (hr) | % loss in colony formation[a] |
|---|---|---|---|
| RA | 1.0 | 120 | 1.7 ± 0.9 |
| 16-23-$D_3$HF | 0.01 | 120 | 26.7 ± 17.3 |
| RA + 16-23-$D_3$HF | 1.0 + 0.01 | 120 | 64.3 ± 18.7 |

[a]mean ± S.E. n = 3

METHOD

Tetrazolium based MTT assay

T47D cells are seeded at densities of $4 \times 10^3$ (cells/well) and seeding the test compound is added to each well. On the second through seventh days, 50 μl 3(4,5-dimethylthiozol-2-yl)-2,5-diphenyltetrazolium bromide is added to each well. The plates are incubated at 37° C. for 2.5 hours. Then, the plates are centrifuged for 5 minutes at 800 ×g, supernantant is aspirated from the wells and 50 μl 100% ethanol is added to each well. The plates are then shaken for 15 minutes to solubilize formazan. A blue color developes in replicating cells. The optical density is measured in anautomatic plate reader at dual wavelength of 570/660 nmn and compared with the optical density of a control. The $IC_{50}$ value reported is the concentration of compound tested at which 50% of cell proliferation is inhibited as determined by the method of Reed and Muench, as described in Reed, L. J., and H. Muench, A Simple Method of Estimating 50% endpoints, Am. J. Hyg. 27:493–497 (1938).

The results are as set forth in Table V below.

TABLE V

| Test Compound | $4 \times 10^3$ cells/well | $8 \times 10^3$ cells/well |
|---|---|---|
| 16-23HF | 1.3 µM | 1.61 µM |
| 1F-16-23HF | 14.2 nM | 22.3 nM |
| 19 nor | 9.0 nM | 15.2 nM |
| $D_3$ | 3.7 nM | 8.9 nM |

The percent loss in colony formation is an index of the irreversible loss of the proliferative potential of the tumor cells and is directly proportional to the tumor kill potency of the Vitamin $D_3$ analog or metabolite, alone or in combination.

The individual components of the method comprising administering trans retinoic acid and a compound selected from the group consisting of 1α,25-dihydroxy-26,27-hexafluorocholecalciferol;

1α,25-dihydroxy-22-ene-26,27-hexafluorocholecalciferol;

1α,25-dihydroxy-26,27-hexafluoro-16-ene-23-yne-cholecalciferol;

1α,25-dihydroxy-23-yne-cholecalciferol;

1α,25-dihydroxy-16-ene-cholecalciferol;

1α,25-dihydroxy-16-ene-23-yne-cholecalciferol;

26,26,26,27,27,27-hexafluoro-25-hydroxy-16-ene-23-yne-cholecalciferol;

26,26,26,27,27,27-hexafluoro-1α-fluoro-25-hydroxy-16-ene-23 -yne-cholecalciferol;

26,26,26,27,27,27-hexafluoro-1α,25-dihydroxy-16-ene-23-yne-19-nor-cholecalciferol;

26,26,26,27,27,27-hexafluoro-25-hydroxy-16-ene-23-yne-19-nor-cholecalciferol; and 26,26,26,27,27,27-hexafluoro-1α-fluoro-25-hydroxy-16-ene-23-yne-19-nor-cholecalciferol may be administered either sequentially or simultaneously in separate or combined pharmaceutical formulations.

The individual components of the method of comprising administering trans retinoic acid and 1α,25-dihydroxycholecalciferol may be administered either sequentially or simultaneously in separate or combined pharmaceutical formulations.

A composition of the invention may be administered by any of the modes by which the components may be administered, for example, orally, intravenously or the like. The dosage regiment may be regulated according to the potency of individual compounds employed, the mode of administration, and the needs of the host mammal depending on factors such as the degree and the severity of the disease state and age and general condition of the host mammal being treated.

In the method of the invention, trans retinoic acid and/or a Vitamin $D_3$ analog or metabolite can be administered in unit dosage forms such as tablets, capsules, pills, powders, granules, sterile parenteral solutions or suspensions, suppositories, transdermal compositions, aerosols and the like. Such dosage forms are prepared according to standard techniques in the art.

The dosages or therapeutically effective amounts utilized in the methods of the invention may be varied depending upon the requirements of the host, the severity of the condition being treated and the particular compound being employed in the method. Determination of dose amount for a particular administration is within the skill of the art. Generally, treatment is initiated at lower dosages and increased as needed by small increments until the optimum effect is reached. Exemplary dosages utilized in the methods of the invention are in the range of 0.00025–0.01 mg Vitamin $D_3$ analog or metabolite per day, with appropriate monitoring of blood calcium levels and adjustment of the dosages as needed. For convenience, the total daily dosage may be administered in divided doses.

Exemplary dosages of trans retinoic acid can be in the range of from about 10 to about 20 mg per day, preferably 14 mg per day. Generally the trans retinoic acid is present in a ratio of from about 100 to about 1000 parts to one part of the Vitamin $D_3$ analog or metabolite.

Oral dosage forms comprising compounds of formula I of the invention may be incorporated in capsules, tablets and the like with one or more pharmaceutically acceptable carrier materials.

Illustrative of the pharmaceutically acceptable carrier materials utilized in the pharmaceutical dosage forms are binders, such as gum tragacanth, acacia, corn starch or gelatin; an excipient, such as, dicalcium phosphate; disintegrating agents, such as, corn starch, potato starch, algenic acid and the like; lubricants, such as, magnesium stearate; sweetening agents, such as, sucrose, lactose or saccharin; flavoring agents, such as, peppermint, oil of wintergreen or cherry. Various other materials may be present as coating or to otherwise modify the physical form of the dosage unit. For instance, tablets may be coated with shellac, sugar or both. A syrup or elixir may contain the active compound, sucrose as a sweetening agent, a dye and a flavoring such as cherry or orange flavor.

Exemplary of formulations which may be utilized in the methods of the invention are:

EXAMPLE 1

| | Capsule Formulation | | |
|---|---|---|---|
| Item | Ingredients | mg/capsule | |
| 1 | 1α,25-dihydroxy-26,27-hexafluorocholecalciferol | 0.005 | 0.010 |
| 2 | Butylated Hydroxyanisole | 0.016 | 0.016 |
| 3 | Butylated Hydroxytoluene | 0.016 | 0.016 |
| 4 | Glycerin | 16.000 | 16.000 |
| 5 | PEG 400 | 143.963 | 143.958 |
| | TOTAL | 160.000 | 160.000 |

Manufacturing Procedure:
Note: Perform all manufacturing steps under a nitrogen atmosphere and protect from light.
1. Warm the mixture of items 4 and 5 to 55° C.
2. Dissolve items 2 and 3 in the solution from Step 1.
3. Dissolve item 1 in the solution from Step 2.

EXAMPLE 2

Capsule Formulation

| Item | Ingredients | mg/capsule |
|---|---|---|
| 1 | 1α,25-dihydroxy-22-ene-26,27-hexafluorocholecalciferol | 0.00025 |
| 2 | Polyethylene glycol 400 | 200.00 |
| 3 | Butylated Hydroxyanisole | 0.100 |
| 4 | Ascorbyl palmitate | 1.00 |

Manufacturing Procedure:
Note: Perform all manufacturing steps under a nitrogen atmosphere and protect from light.
1. Dissolve items 1, 3 and 4 in item 2 and encapsulate.

EXAMPLE 3

Capsule Formulation

| Item | Ingredients | mg/capsule | |
|---|---|---|---|
| 1 | 1α,25-dihydroxy-26,27-hexafluoro-16-ene-23-yne-cholecalciferol | 0.005 | 0.010 |
| 2 | Butylated Hydroxyanisole | 0.016 | 0.016 |
| 3 | Butylated Hydroxytoluene | 0.016 | 0.016 |
| 4 | Neobee M-5 | 159.963 | 159.958 |
| | TOTAL | 160.000 | 160.000 |

Manufacturing Procedure:
Note: Perform all manufacturing steps under a nitrogen atmosphere and protect from light.
1. Warm 10% of item 4 to 55° C.
2. Dissolve items 2 and 3 in the solution from Step 1.
3. Dissolve item 1 in the solution from Step 2.
4. Add the remaining item 4 to the solution from Step 3 and mix well.

EXAMPLE 4

Capsule Formulation

| Item | Ingredients | mg/capsule | |
|---|---|---|---|
| 1 | 1α,25-dihydroxy-16-ene-23-yne-cholecalciferol | 0.005 | 0.010 |
| 2 | Butylated Hydroxyanisole | 0.016 | 0.016 |
| 3 | Butylated Hydroxytoluene | 0.016 | 0.016 |
| 4 | Neobee M-5 | 159.963 | 159.958 |
| | TOTAL | 160.000 | 160.000 |

Manufacturing Procedure:
Note: Perform all manufacturing steps under a nitrogen atmosphere and protect from light.
1. Warm 10% of item 4 to 55° C.
2. Dissolve items 2 and 3 in the solution from Step 1.
3. Dissolve item 1 in the solution from Step 2.
4. Add the remaining item 4 to the solution from Step 3 and mix well.

EXAMPLE 5

Capsule Formulation

| Item | Ingredients | mg/capsule |
|---|---|---|
| 1 | Trans Retinoic Acid | 10.00 |
| 2 | 1α,25-dihydroxy-16-ene-23-yne-cholecalciferol | 0.01 |
| 3 | Purified Beewax | 7.85 |
| 4 | Hydrogenated Soybean Oil | 7.85 |
| 5 | Hydrogenated Vegetable Oil | 31.40 |
| 6 | Butylated Hydroxyanisole | 0.11 |
| 7 | Soybean Oil | 107.28 |
| 8 | Disodium Edetate | 0.50 |
| | TOTAL | 165.00 |

Manufacturing Procedure:
Note: Perform all manufacturing steps under a nitrogen atmosphere and protect from light.
1. Melt items 3, 4 and 5 by hearing at 70° C., and mix well.
2. Dissolve item 6 in the mixture from Step 1.
3. Cool the mixture from Step 2 to 35°–40° C.
4. Add item 8 to the mixture from Step 3 and mix well.
5. Add item 7 to the mixture from Step 4, mix well and cool to room temperature.

Add items 1 and 2 to the mixture from Step 5 and disperse well until a uniform suspension is obtained.

EXAMPLE 6

Capsule Formulation

| Item | Ingredients | mg/capsule |
|---|---|---|
| 1 | Trans Retinoic Acid | 10.000 |
| 2 | 1α,25-dihydroxy-26,27-hexafluoro-16-ene-23-yne-cholecalciferol | 0.00025 |
| 3 | Butylated Hydroxyanisole | 0.016 |
| 4 | Butylated Hydroxytoluene | 0.016 |
| 5 | Glycerin | 16.000 |
| 6 | PEG 400 | 133.86775 |
| | TOTAL | 160.000 |

Manufacturing Procedure:
Note: Perform all manufacturing steps under a nitrogen atmosphere and protect from light.
1. Warm the mixture of items 5 and 6 to 55° C.
2. Dissolve items 3 and 4 in the solution from Step 1.
3. Add items 1 and 2 to the solution from Step 2 and mix well.

EXAMPLE 7

Capsule Formulation

| Item | Ingredients | mg/capsule |
|---|---|---|
| 1 | Trans Retinoic Acid | 10.00 |
| 2 | Purified Beewax | 7.85 |
| 3 | Hydrogenated Soybean Oil | 7.85 |
| 4 | Hydrogenated Vegetable Oil | 31.40 |
| 5 | Butylated Hydroxyanisole | 0.11 |
| 6 | Soybean Oil | 107.24 |
| 7 | Disodium Edetate | 0.50 |
| | TOTAL | 165.00 |

Manufacturing Procedure:

Note: Perform all manufacturing steps under a nitrogen atmosphere and protect from light.
1. Molt items 2, 3 and 4 by heating at 70° C. and mix well.
2. Dissolve item 5 in the mixture from Step 1.
3. Cool the mixture from Step 2 to 35°≠40° C.
4. Add item 7 to the mixture from Step 3 and mix well.
5. Add item 6 to the mixture from Step 4, mix well and cool to room temperature.
6. Add item 1 to the mixture from Step 5 and dispense well until a uniform suspension is obtained.

What is claimed is:

1. A method of treating a host by inducing inhibition of cell proliferation in a solid breast tumor which comprises administering to the host in need of such treatment an effective amount of 1α,25-dihydroxy-26,27-hexafluoro-16-ene-23-yne-cholecalciferol.

2. A method, in accordance with claim 1, wherein the effective amount of 1α,25-dihydroxy-26,27-hexafluoro-16-ene-23-yne-cholecalciferol is in the range of from about 0.00025 mg to about 0.10 mg.

* * * * *